(12) United States Patent
Stephan et al.

(10) Patent No.: US 8,642,812 B2
(45) Date of Patent: Feb. 4, 2014

(54) FRUSTRATED LEWIS PAIR COMPOSITIONS

(75) Inventors: Douglas W. Stephan, Toronto (CA); Gregory C. Welch, Hubley (CA); Jenny S. J. McCahill, Hubley (CA)

(73) Assignee: Stephan Consulting Corporation, Toronto, Ontario (CA)

( * ) Notice: Subject to any disclaimer, the term of this patent is extended or adjusted under 35 U.S.C. 154(b) by 0 days.

(21) Appl. No.: 13/618,790

(22) Filed: Sep. 14, 2012

(65) Prior Publication Data
US 2013/0018207 A1      Jan. 17, 2013

Related U.S. Application Data

(63) Continuation of application No. 12/514,901, filed as application No. PCT/IB2007/004577 on Nov. 14, 2007, now Pat. No. 8,299,284.

(60) Provisional application No. 60/896,557, filed on Mar. 23, 2007, provisional application No. 60/865,684, filed on Nov. 14, 2006.

(51) Int. Cl.
| | | |
|---|---|---|
| B01J 31/24 | (2006.01) | |
| C07F 9/54 | (2006.01) | |
| C07F 9/50 | (2006.01) | |
| C07C 209/52 | (2006.01) | |
| C07C 209/68 | (2006.01) | |
| C07C 209/48 | (2006.01) | |

(52) U.S. Cl.
USPC .......... 568/2; 564/8; 564/9; 564/92; 564/373; 564/385; 502/162

(58) Field of Classification Search
USPC .......... 568/2; 564/8, 9, 92, 373, 385; 502/162
See application file for complete search history.

(56) References Cited

U.S. PATENT DOCUMENTS

| 4,522,932 A | 6/1985 | Mitchell |
| 2001/0049331 A1 | 12/2001 | Chang |

FOREIGN PATENT DOCUMENTS

| WO | WO 99/06449 | 2/1999 |
| WO | 2004113351 | 12/2004 |

OTHER PUBLICATIONS

Welch, Gregory C., et al., Phosphonium-Berate Zwitterions, Anionic Phosphines, and 1 Dianionic Phosphonium-Dialkoxides via Tetrahydrofuran Ring-Opening Reactions; Inorganic Chemistry, vol. 45, No. 2, 2006, pp. 478-480.*
Welch, Gregory C., et aJ., "Reversible, Metal-Free Hydrogen Activation"; Science Nov. 17, 2006; vol. 314; No. 5802, pp. 1124-1126.*
Wetch, Gregory C., et al., "Tuning Lewis acidity using the reactivity of "frustrated Lewis pairs": facile formation of phosphine-boranes and cationic phosphonium-boranes"; The Royal Society of Chemistry~ 2007; Dalton Trans+, 2007, 3407-3414.*
International Search Report for International Patent Application No. PCT/IB2007/004577 issued Nov. 17, 2008.
European Search Report for European Patent Application No. 07 873 357.3 issued Feb. 17, 2012.
Yang, J., et al., "Metal-Free, Organocatalytic Asymmetric Transfer Hydrogenation of α, β-Unsaturated Aldehydes", Angew. Chem. Int. Ed. 2005, 44, 108-110.
Kimura, T., et al., "Novel Metal-Free Hydrogenation of the Carbon-Carbon Double Bond in Azulenoid Enones by Use of Cycloheptatriene and Protic Acid", Organic Letters, 2006, 8(14), 3137-3139.
Chase, P., "Lewis Acid-Catalyzed Hydrogenation: B(C6F5)3-Mediated Reduction of Imines and Nitriles with H2", ChemComm., 2008, 1701-1703.
Spies, P., et al., "Rapid Intramolecular Heterolytic Dihydrogen Activation by a Four-Membered Heterocyclic Phosphane-Borane Adduct", Chem. Commun., 2007, p. 5072-5074.

* cited by examiner

*Primary Examiner* — Shailendra Kumar
(74) *Attorney, Agent, or Firm* — Lowenstein Sandler LLP; Angela Lyon

(57) ABSTRACT

A compound having the formula (I) where each of $R_1$, $R_2$, $R_3$ and $R_4$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{20}$ linear alkyl-, RO—, —NRR', —PRR', —SR, fluoro substituted forms thereof, and perfluoro forms thereof: and $R_5$ is $C_6$-$C_{18}$ aryl-, $C_3$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_3$-$C_{20}$ branched alkyl-, $C_2$-$C_{30}$ linear alkyl-, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S, $R_2$ is a nullity; and M is B, Al, Ga or In.

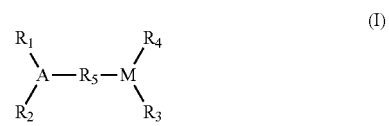

(I)

21 Claims, No Drawings

FRUSTRATED LEWIS PAIR COMPOSITIONS

CROSS-REFERENCE TO RELATED APPLICATIONS

This application is a continuation of U.S. application Ser. No. 12/514,901, filed May 14, 2009, now U.S. 8,299,284, which is a 371 of PCT/IB2007/004577, filed Nov. 14, 2007, which claims priority benefit of U.S. Provisional Applications 60/865,684 filed Nov. 14, 2006; and 60/896,557 filed Mar. 23, 2007 the contents of which are hereby incorporated by reference.

FIELD OF THE INVENTION

The present invention in general relates to compounds and compositions capable of splitting dihydrogen, and in particular to compounds and compositions dissociating dihydrogen and use of said compounds in metal-free hydrogenation. These species are also capable of transfer hydrogenation.

BACKGROUND OF THE INVENTION

The generation and use of molecular hydrogen ($H_2$) are important processes to fundamental chemical transformations and biological functions. The overwhelming majority of systems known to either liberate or react, with $H_2$ involve reaction at a transition metal center. Hydrogenase enzymes, as well as a plethora of synthetic stoichiometric and catalytic reagents for hydrogenation reactions, are based on the processes of oxidative addition and reductive elimination of $H_2$ at metal center. Metal-free systems that either react with or liberate $H_2$ are rare. A unique metal-free hydrogenase from methanogenic archaeas has been shown to catalyze reactions with $H_2$, and theoretical studies suggest the role of a folate-like cofactor in the reversible activation/liberation of $H_2$. Several metal-free systems have been shown to activate $H_2$. For example, main group element-$H_2$ reactions in low temperature matrices are also known.

Hydrogenation is the addition of hydrogen to unsaturated organic compounds. Such reactions are used for the production of a myriad of chemical products worldwide, from large-scale operations including the upgrading of crude oil and the production of bulk commodity materials to the synthesis of a variety of fine chemicals used in the food, agricultural and pharmaceutical industries. The process of hydrogen addition to unsaturated precursors is mediated by either homogeneous or heterogeneous transition metal based catalysts. In the 1960s, the advent of organometallic chemistry gave rise to homogeneous transition metal based hydrogenation catalysts for a variety of substrates. The operation of these catalysts hinges on the key step of oxidative addition of hydrogen. More recently, transition metal systems that effect heterolytic cleavage of hydrogen at a metal center have been uncovered. In these cases, a metal hydride is formed with concurrent protonation of an amido ligand.

Non-transition metal catalysts for hydrogenation reactions are all but unknown. KOtBu has been shown to act as a catalyst effecting the addition of $H_2$ to benzophenone under forcing conditions of 200° C. and greater than 100 bar $H_2$. Organocatalysts have been developed for hydrogenations of enones and imines; however, such systems do not employ $H_2$ directly but rather a surrogate such as a Hantzsch ester as the stoichiometric source of hydrogen. The development of non-metal hydrogenation catalysts hinges on the discovery of systems that react cleanly with $H_2$, but few are known. Power and coworkers reported the hydrogenation of $Ge_2$-alkyne analogues to give a mixture of $Ge_2$ and primary germane products. J. W. Yang. M. T. Hechavarria Fonseca, B. List, Angew. Chem. 2004, 116, 6829; Angew. Chem. Int. Ed. 2004, 43, 6660. G. H. Spikes, J. C. Fettinger, P. P. Power, J. Am. Chem. Soc. 2005, 127, 12 232. It should be noted that non-transition metal systems have been shown to effect hydrogenation under more forcing conditions. For example, DeWitt, Ramp and Trapasso demonstrated hydrogenation with $iPr_3B$ under 67 atm 1000 psi) $H_2$ at 220° C. E. J. DeWitt, F. L. Ramp, L. E. Trapasso, *J. Am. Chem. Soc.* 1961, 83, 4672-4672; F. L. Ramp, E. J. DeWitt, L. E. Trapasso, *Org. Chem.,* 1962, 27, 4368-4372). Similarly, Haenel and coworkers (E. Osthaus, M. W. Haenel in *Coal Science and Technology*, Vol. 11 Elsevier, Amsterdam, 1987, pp. 765-768 (Proc. 1987 Intern. Conf. Coal Sci., Eds.: J. A. Moulijn, K. A. Nater, H. A. G. Chermin); M. Yalpani, R. Köster, M. W. Haenel, Erdoel Kohle, Erdgas, *Petrochem.* 1990, 43, 344-347; M. W. Haenel, J. Narangerel, U.-B. Richter, A. Rufinska, *Angew. Chem.* 2006, 118, 1077-1082; *Angew. Chem. Int. Ed.* 2006, 45, 1061-1066; M. W. Haenel, J. Narangerel, U.-B. Richter, A. Rufinska, *Prep. Pap. Am. Chem. Soc., Div. Fuel Chem.* 2006, 51(2), 741-742) among others showed hydrogenation of coal under almost 15 MPa and 280-350° C. using $BI_3$ or alkyl boranes. M. Yalpani, T. Lunow, R. Köster, *Chem. Ber.* 1989, 122, 687-693; (b) M. Yalpani, R. Köster. *Chem. Ber.* 1990, 123, 719-724. As well, superacid systems have also been shown to effect hydrogenation of alkenes using $H_2$ pressures of at least 35 atm. M. Siskin, *J. Am. Chem. Soc.* 1974, 96, 3641; (b) J. Wristers. *J. Am. Chem. Soc.* 1975, 97, 4312.

The ability to dissociate dihydrogen represents a reaction of considerable importance in fields including hydrogenation of ethenically unsaturated feed stocks, chemical fuel storage, hydrogen purification, and hydrogen getters that prevent hydrogen levels from building beyond a preselected threshold. Traditionally, dihydrogen dissociation has involved the use of metal catalysts and in particular palladium. Conventional catalysts inclusive of metal have a number of limitations that include high material cost, high density, the heterogeneous nature of such catalysts relative to liquid phase reactants, and contamination of resultant products with metal catalysts.

Thus, there exists a need for a hydrogen dissociation catalyst that is independent of metal. Additionally, a catalyst capable of operating as a homogeneous catalyst would afford considerable operational advantages. Further, these hydrogen catalysts operate efficiently at lower or comparable temperatures to those used for existing metal based hydrogenation catalysts.

SUMMARY OF THE INVENTION

A compound is provided that is operative as a hydrogenation catalyst. The compound is capable of homogenous liquid phase catalysts exclusive of a noble metal. A compound has the formula:

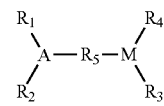

I where each of $R_1$, $R_2$, $R_3$ and $R_4$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least, one $C_1$-$C_{20}$ alkyl substituent, $C_4$-$C_{20}$ branched alkyl-, $C_{16}$-

$C_{30}$ linear alkyl-, RO—, —NRR', —PRR', —SR, fluoro substituted forms thereof, and perfluoro forms thereof; and $R_5$ is $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_3$-$C_{20}$ branched alkyl-, $C_2$-$C_{30}$ linear alkyl-, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S or O, $R_2$ is a nullity; and M is B, Al, Ga or In.

A composition operative as a hydrogenation catalyst includes a compound having the formula:

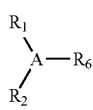

II where each of $R_1$ and $R_2$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms thereof, and perfluoro forms thereof; $R_6$ is $C_1$-$C_{30}$ alkyl-, $C_6$-$C_{18}$ aryl-, $C_5$-$C_8$ cycloalkyl-, RO—, —NRR', —PRR', —SR, a fluoro substituted forms thereof, and perfluoro substituted form thereof, H or F; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S or O, $R_2$ is a nullity; in fluid communication with a composition having the formula:

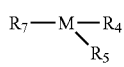

III where each of $R_4$, $R_5$ and $R_7$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; and M is B, Al, Ga or In; or a composition of the formula:

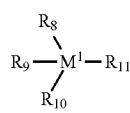

V where $M^1$ is Ti, Zr or Hf; each of $R_8$, $R_9$ and $R_{10}$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, amide, alkoxide, phenoxide, phosphinimide, cyclopentadienyl, indenyl, fluorenyl derivatives, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; and $R_{11}$ is $C_1$-$C_{20}$ alkyl linear or branched with the proviso that $R_{11}$ is a better leaving group than any of $R_8$, $R_9$ or $R_{10}$ under nucleophic attack by a hydrogen or other alkyl abstracting agents to yield a cationic $M^1$ species.

A compound is also provided that is an addition reaction product of a compound of formula I and dihydrogen ($H_2$). The compound has the formula:

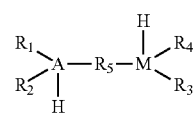

IV where each of $R_1$, $R_2$, $R_3$ and $R_4$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms thereof, and perfluoro forms thereof; and $R_5$ is $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_3$-$C_{20}$ branched alkyl-, $C_2$-$C_{30}$ linear alkyl-, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl subsequent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S, $R_2$ is a nullity; and M is B, Al, Ga or In.

A process of catalytic hydrogenation of a substrate comprising: independently compound I, a mixture of II and III, compound III, a mixture of II, III-V, compound IV, or compound VI together with dihydrogen and solvent form a catalyst whereby hydrogenation of a substrate is effected.

DETAILED DESCRIPTION OF THE PREFERRED EMBODIMENTS

The present invention has utility as compounds and compositions capable of dissociating dihydrogen and reversibly binding hydrogen atoms. In addition to dihydrogen dissociation, a sacrificial dihydrogen source such as primary or secondary amines, primary or secondary phosphines, alcohols and thiols are also is operative according to the present invention to reduce substrates. According to the present invention, a compound is provided that is the reaction product of a sterically hindered Lewis acid with a sterically hindered Lewis base via an intermediate linker group therebetween. The prototypical form of an inventive compound I is a reaction product of linker separated sterically hindered phosphine and a sterically hindered borane. An inventive compound has the formula:

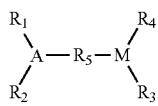

where each of $R_1$, $R_2$, $R_3$ and $R_4$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{30}$ linear alkyl-, RO—, —NRR', —PRR', —SR, fluoro substituted forms thereof, and perfluoro forms thereof; and $R_5$ is $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_3$-$C_{20}$ branched alkyl-, $C_2$-$C_{30}$ linear alkyl-, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S or O, $R_2$ is a nullity; and M is B, Al, Ga or In.

A bimolecular composition according to the present invention capable of dissociating hydrogen and reversibly binding hydrogen atoms includes in a mixture of a phosphine and a borane incapable of reaction owing to steric hindrance. Sterically hindered phosphine is readily replaced with a nitrogen, oxygen, or sulfur analog as shown in formula II. Sterically hindered borane is readily replaced with an aluminum, gallium, or indium analog as shown in formula III. Lesser sterically hindered systems exhibit reactivity at temperatures dependent on the nature of the compounds. The mixture of sterically hindered Lewis base and Lewis acid compounds operative herein have the formulae II and III, respectively:

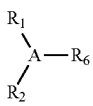

where each of $R_1$ and $R_2$ is independently $C_6$-$C_{18}$ is aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $Cl_6$-$C_{30}$ linear alkyl-, RO—, —NRR', —PRR', —SR, fluoro substituted forms thereof, and perfluoro forms thereof; $R_6$ is $C_1$-$C_{30}$ alkyl-, $C_6$-$C_{18}$ aryl-, $C_5$-$C_8$ cycloalkyl-, RO—, —NRR', —PRR', —SR, a fluoro substituted form thereof, a perfluoro substituted form thereof, H or F; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_1$-$C_{30}$ linear alkyl-, fluoro substituted forms thereof, and perfluoro forms thereof; A is N, P, S, or O with the proviso that when A is S or O, $R_2$ is a nullity.

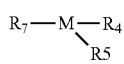

where each of $R_4$, $R_5$ and $R_7$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $Cl_6$-$C_{18}$ linear alkyl-, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; and M is B, Al, Ga or In. In a particular embodiment a sterically hindered perfluorinated composition of formula III has hydrogen catalytic activity independent of the presence of a compound of formula II.

A compound of the formula is also provided that is reversibly convened into the compound of formula I through loss of two hydrogen atoms. The compound has the formula:

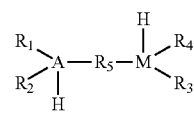

where each of $R_1$, $R_2$, $R_3$ and $R_4$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_{16}$-$C_{20}$ linear alkyl-, RO—, —NRR', —PRR', —SR, fluoro substituted forms thereof, and perfluoro forms thereof; and $R_5$ is $C_6$-$C_{18}$ aryl-, $C_5$-$C_8$ cycloalkyl-, $C_3$-$C_{20}$ branched alkyl-, $C_2$-$C_{30}$ linear alkyl-, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; A is N, P, S, or O with the proviso that when A is S, $R_2$ is a nullity; and M is B, Al, Ga or in.

In an alternate embodiment, hydrogenation occurs through the interaction of a composition of formula II with a transition metal cation of Ti, Zr, or Hf when A is P or N. The transition metal cation is generated in situ by alkyl group abstraction from an organometallic composition of the formula:

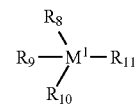

where $M^1$ is Ti, Zr or Hf; each of $R_8$, $R_9$ and $R_{10}$ is independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, amide, alkoxide, phenoxide, phosphinimide, cyclopentadienyl, indenyl, fluorenyl derivatives, RO—, —NRR', —PRR', —SR, fluoro substituted forms thereof, and perfluoro forms thereof; where R and R' are each independently $C_6$-$C_{18}$ aryl-, $C_5$-$C_8$ cycloalkyl-, $C_6$-$C_{18}$ aryl having at least one $C_1$-$C_{20}$ alkyl substituent, $C_5$-$C_8$ cycloalkyl having at least one $C_1$-$C_{20}$ alkyl substituent, $C_4$-$C_{20}$ branched alkyl-, $C_2$-$C_{30}$ linear alkyl-, fluoro substituted forms thereof, and perfluoro forms thereof; and $R_{11}$ is $C_1$-$C_{20}$ alkyl linear or branched with the proviso that $R_{11}$ is a better leaving group than any of $R_8$, $R_9$ or $R_{10}$ under nucleophic attack by a hydrogen or other alkyl abstracting agents to yield a cationic $M^1$ species.

The present invention compounds and mixtures of compounds are effective as hydrogenation catalysts for performing reactions illustratively including those provided in Table 1. The compositions and compounds of formulae I-V are operative in hydrogenation catalysis in a neat liquid substrate, in a solution containing substrate, or applied as coating on an inert support.

TABLE 1

Substrate hydrogenation to products according to the present invention.

| Substrates | Products |
| --- | --- |
| ketimines | amines |
| ketene-imines | amines |
| aldimines | amines |
| nitriles | amines |
| aziridines | amines |
| olefins | hydrocarbon |
| ketones | alcohols |
| aldehydes | alcohols |
| borazines | borane-amine adducts |
| acetylene | hydrocarbon |
| enols | alcohols |
| enamines | amines |
| ketenes | alcohol |
| allenes | alkanes |
| esters | alcohols |
| epoxides | alcohols |
| isocyanides | amines |
| lactones | diols |

In our recent work, we have been studying systems in which steric demands preclude classical donor-acceptor interactions. Such "frustrated Lewis pairs" prompt unique reactivity. Herein, we demonstrate that although phosphines and boranes are not known to react individually with olefins, "frustrated Lewis pairs" react with olefins to give alkyl-linked phosphonium borates in a regioselective fashion. A bromobenzene solution containing the combination of $tBu_3P$ and $B(C_6F_5)_3$ was purged with ethylene and stored under 1 atm of ethylene at 25° C. Over the course of several hours, a colorless precipitate 1 formed. This was isolated by filtration in 63% yield. The $^{31}P\{^1H\}$ NMR spectrum of 1 showed a singlet resonance at 50.1 ppm while the corresponding $^{11}B\{^1H\}$ NMR signal was observed at −13.3 ppm. The $^1H$ NMR spectrum of 1 showed broad multiplets at 1.69-1.94 ppm. These data confirm the presence of phosphonium and borate fragments linked by $C_2H_4$ thus affirming the formulation of 1 as $[tBu_3P(C_2H_4)B(C_6F_5)_3]$ (Scheme 1). An X-ray crystallographic study confirmed the proposed zwitterionic formulation, establishing unambiguously that the phosphine and borane add to opposite ends of ethylene forming pseudo-tetrahedral centers in both cases.

Scheme 1. Inter- and intramolecular addition of frustrated phosphine/borane pairs to olefins.

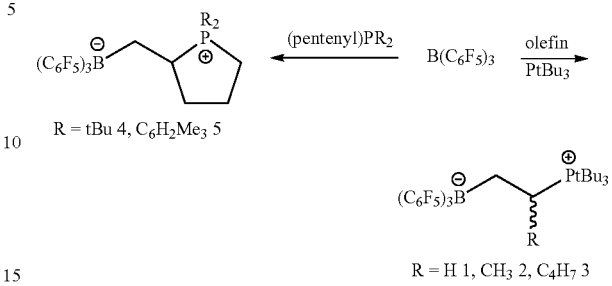

$R = tBu\ 4, C_6H_2Me_3\ 5$ $R = H\ 1, CH_3\ 2, C_4H_7\ 3$

Scheme 1. Inter- and intramolecular addition of frustrated phosphine/borane pairs to olefins.

Similar intermolecular reactions of propylene and 1-hexene with $tBu_3P$ and $B(C_6F_5)_3$, afforded the new species 2 and 3 which were subsequently isolated in 63 and 55% yield. These products exhibited $^{31}P\{^1H\}$ and $^{11}B\{^1H\}$ NMR signals at 56.9, and 58.3 and −11.6 and −13.0 ppm, respectively, consistent with the presence of phosphonium and borate fragments similar to 1. The $^1H$ and $^{19}F$ NMR spectra reveal the expected resonances for propyl and hexyl groups and inequivalent $C_6F_5$ groups consistent with the generation of a chiral center from the prochiral olefins. Two dimensional $^{13}C$-$^1H$ NMR correlation spectra were used to establish resonance assignments. These data supported a regiochemistry of addition in which P-atom adds to the secondary olefinic carbon while the B-atom adds to the terminal methylene group, prompting the formulations of 2 and 3 as $[tBu_3P(CH(R)CH_2B(C_6F_5)_3]$ (R=Me, $C_4H_9$), respectively. X-ray crystallographic study of 3 confirmed this regiochemistry of addition.

These "frustrated Lewis pairs" can also react with olefins in an intramolecular fashion. The olefinic derivatives of sterically demanding phosphines of the form $CH_2=CH(CH_2)_3PR_2$ (R=tBu, $C_6H_2Me_3$) were prepared via conventional methods. Stoichiometric reactions with $B(C_6F_5)_3$ were monitored by $^{31}P$ NMR spectroscopy. These data reveal no evidence of phosphine-borane adduct formation. Rather, the reaction proceeds in $CH_2Cl_2$ at 25° C. to give species 4 and 5 in 94 and 52% isolated yields respectively. The $^{31}P\{^1H\}$ NMR spectrum of 4 and 5 showed singlet resonances at 62.4 and 52.8 ppm while the corresponding $^{11}B\{^1H\}$ NMR signals were observed at −13.8 and −13.7 ppm, respectively. $^{19}F$ NMR spectra for 4 and 5 confirmed the presence of $C_6F_5$ groups. These data together with the $^1H$ and $^{13}C$ NMR data support the formulation of 4 and 5 as the cyclized phosphonium borate $[R_2PCH(C_2H_4)CH_2B(C_6F_5)_3]$ (R=tBu 4, $C_6H_2Me_3$ 5) (Scheme 1).

In summary, sterically frustrated pairs of phosphines and the borane, $B(C_6F_5)_3$ exhibit unique reactivity with olefins, affording both intermolecular additions as well as intramolecular cyclizations. The utility of this remarkably simple system for olefin functionalization, as well as the unique reactivity of "frustrated Lewis pairs" are the subject of ongoing study.

The present invention is further detailed with respect to the following nonlimiting examples.

EXAMPLE 1

General Catalysis Procedure

The catalyst (0.1-20 mol %) is weighed into a 50 ml round bottomed Schlenk flask and slurried in toluene (2 ml). The reaction is charged with H$_2$. The slurry is then allowed to equilibrate at the desired temperature under an atmosphere of H$_2$ with rapid stirring. A solution of substrate (1.0 mmol) in toluene (2 ml) is added via syringe. Reaction time and temperature vary with substrate. In all cases, the crude mixtures of the completed reactions are pure to the limits of NMR spectroscopy. The product is purified by all volatiles being removed in vacuo trap to trap vacuum distillation or filtration through a small plug of silica to remove residual catalyst.

EXAMPLE 2

Conversion of N-benzylidine-tert-butyl amine to benzyl-tert-butylamine with tBu$_2$PH—C$_6$F$_4$—BH(C$_6$F$_5$)$_2$ In a glove box, tBu$_2$PH—C$_6$F$_4$—BH(C$_6$F$_5$)$_2$ (0.033 g, 0.05 mmol) is weighed into a 50 ml round bottomed Schlenk flask equipped with a small stir bar and slurried in toluene (2 ml). The reaction is attached to a vacuum/H$_2$ line and freeze-pump-thaw cycled three times. The slurry is then allowed to equilibrate at 80° C. under an atmosphere of H$_2$ with rapid (500 rpm) stirring. A solution of N-benzylidine-tert-butyl amine (0.161 g, 1.0 mmol) in toluene (2 ml) is added via syringe. The reaction is periodically monitored by thin layer chromatography (silica, eluent: 1:5 ethyl acetate/hexanes) and $^1$H NMR spectroscopy and is complete in 1 hour. The solvent is removed in vacuo and the product benzyl-tert-butylamine is purified by trap to trap vacuum distillation. Isolated yield 0.128 g (79%).

EXAMPLE 3

Alternate General Catalysis Procedure

The catalyst (0.01-0.20 mmol) and substrate (1 mmol) are weighed into a 100 ml round bottomed glass flask equipped with a Kontes valve. Solvent (4 ml) is added, the reaction transferred to a vacuum/H$_2$ line and the mixture is freeze-pump-thaw cycled three times. The mixture is cooled to −196° C. (liquid N$_2$) and 1 atm. H$_2$ is introduced. The flask is sealed, the reaction is placed in a preheated bath and rapidly stirred. Reaction time and temperature vary with substrate. In all cases, the crude reaction mixtures are of the completed reactions are pure to the limits of NMR spectroscopy. The product is purified by removal of all volatile in vacuo and trap to trap vacuum distillation or filtration through a small plug of silica to remove residual catalyst.

EXAMPLE 4

Conversion of cis-1,2,3-triphenylaziridine to N-1,2 diphenylethyl-N-phenyl amine with tBu$_2$PH(C$_6$F$_4$)BH(C$_6$F$_5$)$_2$ In a glove box, tBu$_2$PH(C$_6$F$_4$)BH(C$_6$F$_5$)$_2$ (0.33 g, 0.05 mmol) and cis-1,2,3-triphenylaziridine (0.271 g, 1.0 mmol) were weighed into a 100 ml round bottomed glass flask equipped with a Kontes valve and a magnetic stirbar. Toluene (4 ml) is added, the reaction transferred to a vacuum/H$_2$ line and the mixture is freeze-pump-thaw cycled three times. The mixture is cooled to −196° C. (liquid N$_2$) and 1 atm. H$_2$ is introduced. The flask is sealed, the reaction is placed in a 120° C. preheated bath and rapidly (500 rpm) stirred. The reaction is periodically monitored by $^1$H NMR spectroscopy and is complete in 2 hours. The reaction mixture is poured onto a small plug of silica and eluted with 2:1 hexanes/ethyl acetate (50 ml). The solvent is removed in vacuo and the product N-1,2-diphenylethyl-N-phenyl amine isolated. Yield: 0.269 g (98%)

COMPARATIVE EXAMPLE

B(C$_6$F$_5$)$_3$-Only Reductive Catalysis

In the glovebox, a substrate (1 mmol) per Table 2, B(C$_6$F$_5$)$_3$ (26 mg, 0.05 mmol, 5 mol %) and dry toluene (4 ml) are weighed into a 100 ml round bottomed flask equipped with a sealable Teflon tap and small magnetic stirbar. The reaction is then attached to a double manifold H$_2$/vacuum line and degassed (freeze-pump-thaw cycle×3). The reaction is cooled to −196° C. (liquid N$_2$) and 1 atm. H$_2$ is introduced. The flask is sealed and warmed to room temperature. The reaction is then placed in an oil bath heated to the desired temperature and stirred at 500 rpm. At 120° C., the H$_2$ pressure is ~5 atm. Aliquots are obtained at periodic intervals by rapidly cooling the reaction in a water bath and venting the H$_2$ pressure. Samples are taken by pipette in the glove box. The reaction is re-pressurized using the above procedure. Upon full conversion, the reaction is poured onto a 10 cm plug of silica (200 mesh) and eluted with 2:1 hexanes/ethyl acetate (200 ml). If the amine is not fully soluble in the reaction mixture or the hexanes/ethyl acetate solvent, CH$_2$Cl$_2$(3×5 ml) is used to wash the reaction vessel. The collected solvent is removed in vacuo to obtain the product in the time and yield shown in Table 2.

TABLE 2

B(C$_6$F$_5$)$_3$-only catalyzed reductions. Conditions: 120° C., toluene, ~5 atm. H$_2$, 500 rpm stir rate.

$$\text{substrate} \xrightarrow{\text{5 mol \% B(C}_6\text{F}_5)_3} \text{product}$$

| substrate | time | isolated yield | product |
|---|---|---|---|
|  | 2 h$^a$ | 89% | 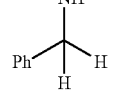 |
|  | 1 h | 99% | 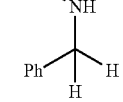 |
|  | 41 h | 94% | 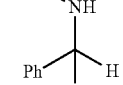 |
|  | 1 h | 98% | 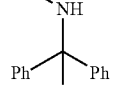 |

TABLE 2-continued

B(C$_6$F$_5$)$_3$-only catalyzed reductions. Conditions: 120° C., toluene, ~5 atm. H$_2$, 500 rpm stir rate.

substrate $\xrightarrow{\text{5 mol \% B(C}_6\text{F}_5)_3}$ product

| substrate | time | isolated yield | product |
|---|---|---|---|
| Dipp-N=C(Ph)Me | 8 h | 94% | Dipp-NH-CH(Ph)Me |
| Dipp-N=C(tBu)Me | 48 h | 0% | Dipp-NH-CH(tBu)Me |
| Ph-aziridine (Ph,Ph) | 2 h | 95% | Ph-CH(Ph)-CH(NHPh)-Ph |

$^a$conditions. 1 atm. H$_2$, 80° C.

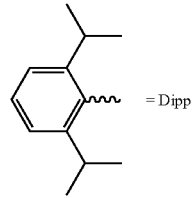 = Dipp

EXAMPLE 5

B(C$_6$F$_5$)$_3$ and Phosphine Reductive Catalysis

In the glovebox, a substrate (1 mmol) per Table 3, is reacted in the presence of P(2,4,6-Me$_3$C$_6$H$_2$)$_3$ (19 mg 0.05 mmol, 5 mol %) or PtBu$_3$ (10 mg, 0.05 mmol, 5 mol %) according to the procedure of the Comparative Example. As shown in Table 3, more efficient reaction with the sterically hindered phosphine (formula II) is noted for the imine PhCH(N)SO$_2$Ph and MeCN—B(C$_6$F$_5$)$_3$ reacts when no reductive catalysis is noted absent the phosphine (formula II).

TABLE 3

Comparison of B(C$_6$F$_5$)$_3$-only and B(C$_6$F$_5$)$_3$/PMes$_3$ catalyzed reductions. Conditions: 120° C., toluene, ~5 atm. H$_2$, 500 rpm stir rate.

substrate $\xrightarrow[\text{phosphine}]{\text{5 mol \% B(C}_6\text{F}_5)_3}$ product

| substrate | phosphine (mol %) | time | isolated yield | product |
|---|---|---|---|---|
| PhSO$_2$-N=CH-Ph | — | 41 h | 94% | PhSO$_2$-NH-CH$_2$-Ph |
|  | PMes$_3$ (5) | 8 h | 98% |  |
| Me—≡N—B(C$_6$F$_5$)$_3$ | — | 48 h | 0% | Me-CH$_2$-NH$_2$—B(C$_6$F$_5$)$_3$ |
|  | PMes$_3$ (5) | 49 h | 91% |  | mesityl = Mes

EXAMPLE 6

Imine Nitrite Reduction

In a glove box, a 100 mL glass bomb equipped with a small stir bar and a Teflon screw tap is charged with imine (1 mmol), catalyst (0.05 mmol, 5 mol %), and dry toluene (4 ml). The reaction is transferred to the vacuum/H$_2$ line and is degassed three times with a freeze-pump-thaw cycle. The reaction flask is cooled to −196° C., 1 atm of H$_2$ is introduced, and the flask then sealed and warmed to room temperature. The reaction is placed in a preheated oil bath and stirred at 500 rpm; at 120° C., this gave an H$_2$ pressure of about 5 atm. To take aliquots, the reaction is cooled rapidly in an ice bath, vented to release the H$_2$ pressure, and taken into a glove box. For the catalyst (2,4,6-Me$_3$C$_6$H$_2$)$_2$ PH(C$_6$H$_4$) BH(C$_6$F$_5$)$_2$ (denoted as compound 1) and (tert-butyl)$_2$ PH(C$_6$H$_4$) BH(C$_6$F$_5$)$_2$ (denoted as compound 2), the following products are obtained in the time and yield shown in Table 4.

TABLE 4

Imine and nitrile reduction by catalyst compositions 1 and 2.

| Entry | Substrate | Catalyst | T [8 C.] | t [h] | Yield [%] | Product |
|---|---|---|---|---|---|---|
| 1 | Ph(H)C=NtBu | 1[b] | 80 | 1 | 79 | PhCH$_2$NHtBu |
| 2 | Ph(H)C=NtBu | 2[b] | 80 | 1 | 98 | PhCH$_2$NHtBu |
| 3 | Ph(H)C=NSO$_2$Ph | 1 | 120 | 10.5 | 97 | PhCH$_2$NHSO$_2$Ph |
| 4 | Ph(H)C=NSO$_2$Ph | 2 | 120 | 16 | 87 | PhCH$_2$NHSO$_2$Ph |
| 5 | Ph(H)C=NCHPh$_2$ | 1 | 140 | 1 | 88 | PhPhCH$_2$NHCHPh$_2$ |
| 6 | Ph(H)C=NCH$_2$Ph | 1 | 120 | 48 | 5[c] | PhCH$_2$NHCH$_3$Ph |
| 7 | Ph(H)C=NCH$_2$Ph(B(C$_6$F$_5$)$_3$) | 1 | 120 | 46 | 57 | PhCH$_2$NHCH$_2$Ph(B(C$_6$F$_4$)$_3$) |
| 8 | MeCNB(C$_6$F$_5$)$_3$ | 1 | 120 | 24 | 75 | MeCH$_2$NH$_2$B(C$_6$F$_5$)$_3$ |
| 9 | PhCNB(C$_6$F$_5$)$_3$ | 1 | 120 | 24 | 84 | PhCH$_2$NH$_2$B(C$_6$F$_5$)$_3$ |

TABLE 4-continued

Imine and nitrile reduction by catalyst compositions 1 and 2.

| Entry | Substrate | Catalyst | T [8 C.] | t [h] | Yield [%] | Product |
|---|---|---|---|---|---|---|
| 10 | $(CH_2CH_2CNB(C_6F_5)_3)_2$ | 1[d] | 120 | 48 | 99 | $(CH_2CH_2CH_2NH_2B(C_6F_5)_3)_2$ |
| 11 | PhCHCHPhNPh | 1[d] | 120 | 1.5 | 98 | $PhCH_2CHPhNHPh$ |

[a]Standard conditions: 5 mol % catalyst, 4 ml. roluene, ca. 5 atm $H_2$.
[b]1 atm $H_2$.
[c]Determined by 1H NMR spectroscopy.
[d]10 mol % catalyst.

EXAMPLE 7

Synthesis of $[R_3P(C_6F_4)BF(C_6F_5)_2]$ R=isopropyl (Denoted as Compound 3), R=cyclohexyl (Denoted as Compound 4), of $[R_2PH(C_6F_4)BF(C_6F_5)_2]$ R=tert-butyl (Denoted as Compound 5) and (2,4,6-$Me_3C_6H_2$) (Denoted as Compound 6)

These compounds are prepared in a similar fashion. A clear yellow solution of $B(C_6F_5)_3$ (0.500 g, 0.98 mmol) and i-$Pr_3P$ (0.156 g, 0.98 mmol) or molar equivalent of $(C_6H_{11})_3P$, (t-Bu)$_3P$, or (2,4,6-$Me_3C_6H_2)_3P$ in toluene (20 mL) is allowed to stir for 12 h at 25° C. during which time a white precipitate formed. Pentane (10 mL) is added, the mixture filtered and dried in vacuo for 1 h. In the instance of (2,4,6-$Me_3C_6H_2)_3P$ stirring look place in refluxing toluene. The product is collected as a while solid.

EXAMPLE 8

Synthesis of $[R_3P(C_6F_4)BH(C_6F_5)_2]$ R=isopropyl (Denoted as Compound 7), R=cyclohexyl (Denoted as Compound 8), of $[R_2PH(C_6F_4)BH(C_6F_5)_2]$ R=t-Bu (Denoted as Compound 9) and (2,4,6-$Me_3C_6H_2$) (Denoted as Compound 10)

To a solution of compound 3 (0.400 g, 0.600 mmol) or a molar equivalent of compounds 4, 5 or 6 dissolved in $CH_2Cl_2$ (10 ml.) is added $(CH_3)_2SiHCl$ (0.66 mL, 6.00 mmol) via syringe. The reaction is allowed to stir 12 h, during which time a precipitate forms. All volatiles are removed in vacuo to give the product as a white solid.

EXAMPLE 9

Synthesis of $[R_3P(C_6F_4)B(C_6F_5)_2][B(C_6F_5)_4]$ R=isopropyl (Denoted as Compound 11), R=cyclohexyl (Denoted as Compound 12), of $[R_2PH(C_6F_4)B(C_6F_5)_2][B(C_6F_5)_4]$ R=t-Bu (Denoted as Compound 13) and (2,4,6-$Me_3C_6H_2$) (Denoted as Compound 14)

An orange solution of $[Ph_3C][B(C_6F_5)_4]$ (0.420 g, 0.456 mmol) in $CH_2Cl_2$ (2 mL) is added to a slurry of compound 7 (0.300 g, 0.457 mmol) or molar equivalent of 8, 9, or 10 in $Ch_2Cl_2$ (5 mL) to give a faint yellow solution. The reaction is allowed to stir tor 30 min and the volatiles are removed in vacuo. Pentane (5 mL) is added and the mixture filtered and washed with toluene (2 mL) and pentane (3×2 mL) to give an off white solid.

EXAMPLE 10

Synthesis of $R_2P(C_6F_4)B(C_6F_5)_2$ R=tert-butyl (Denoted as Compound 15), (2,4,6-$Me_3C_6H_2$) (Denoted as Compound 16)

A 20 mL vial is charged with compound 5 (0.099 g, 0.150 mmol) or a molar equivalent of composition 6, toluene (10 mL) and diethyl ether (1 mL), forming a white slurry. The mixture is cooled to −35° C. and 3.0 M MeMgBr in diethyl ether (0.060 mL, 0.180 mmol) is added via syringe. Immediate formation of a clear yellow solution is observed. The reaction is allowed to warm to room temperature and stirred for 12 h. All volatiles are removed in vacuo and the product extracted with hexanes (3×5 mL) and filtered through celite. The solvent is removed in vacuo to give a yellow solid.

EXAMPLE 13

Conversion of cis-1,2,3-triphenylaziridine to N-1,2-diphenylethyl-N-phenyl amine with B(C6F5)3 and (2,4,6-$Me_3C_6H_2)_3P$ In a glovebox, cis-1,2,3-triphenylaziridine (1 mmol), $B(C_6F_5)_3$ (6.05 mmol) and (2,4,6-$Me_3$ $_{C_6}H_2)_3P$ (0.05 mmol) are reacted according to the procedure of the Comparative Example to yield N-1,2-diphenylethyl-N-phenyl amine.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process comprising:
combining, in fluid communication: (a) an addition reaction reagent that comprises at least one terminal olefin moiety; (b) a sterically hindered Lewis acid comprising B, Al, Ga, In, Ti, Zr or Hf; and (c) a sterically hindered Lewis base comprising N, P, S, or O; and
obtaining an addition reaction product, wherein the sterically hindered Lewis base is a compound of formula II and the sterically hindered Lewis acid is a compound of formula III, wherein the compounds of formula II and III are:

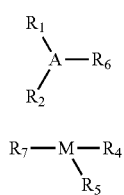

where
- $R_1$, $R_2$, $R_4$, $R_5$, and $R_7$ are independently: $C_8$-$C_{10}$ aryl; $C_6$-$C_8$ cycloalkyl; $C_8$-$C_{10}$ aryl having at least one $C_1$-$C_{20}$ alkyl substituent; $C_5$-$C_8$ cycloalkyl having at least one $C_1$-$C_{20}$ alkylsubstituent; $C_4$-$C_{20}$ branched alky; $C_{16}$-$C_{20}$ linear alkyl; —OR; —NRR'; —PRR'; or —SR;
- $R_6$ is $C_1$-$C_{38}$ alkyl; $C_6$-$C_{38}$ aryl; $C_8$-$C_{30}$ cycloalkyl; —OR; —NRR'; —PRR'; —SR; H; or F;
  - R and R' are, independently: $C_6$-$C_{10}$ aryl; $C_6$-$C_8$ cycloalkyl; $C_6$-$C_{18}$ aryl having at least one $C_1$-$C_{20}$ alkyl substituent; $C_6$-$C_8$ cycloalkyl having at least one $C_1$-$C_{20}$ substituent; $C_4$-$C_{20}$ branched alkyl; or $C_8$-$C_{20}$ linear alkyl;
- A is: N; P; S; or O; with the proviso that when A is S or O, $R_2$ is a nullity; and
- M is: B, Al, Ga, In, Ti, Zf or Hf.

2. A process comprising:
combining, in fluid communication: (a) an addition reaction reagent that comprises at least one terminal olefin moiety and a sterically hindered Lewis base comprising N, P, S, or O; and (b) a sterically hindered Lewis acid that is a compound of formula III; and
obtaining an addition reaction product;
wherein the compound of formula III is:

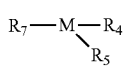

where
- $R_4$, $R_5$, and $R_7$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;
- R and R' are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; or $C_2$-$C_{30}$ linear alkyl; and
- M is: B, Al, Ga, In, Ti, Zr or Hf.

3. A process comprising:
combining, in fluid communication: (a) an addition reaction reagent that comprises at least one terminal olefin moiety and a sterically hindered Lewis acid comprising B, Al, Ga, In, Ti, Zr or Hf; and (b) a sterically hindered Lewis base that is a compound of formula II; and
obtaining an addition reaction product;
wherein the compound of formula II is:

where
- $R_1$, and $R_2$ are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; $C_{16}$-$C_{30}$ linear alkyl; —OR; —NRR'; —PRR'; or —SR;
- $R_6$ is $C_1$-$C_{30}$ alkyl; $C_6$-$C_{18}$ aryl; $C_5$-$C_8$ cycloalkyl; —OR; —NRR'; —PRR'; —SR; H; or F;
- R and R' are, independently: $C_6$-$C_{18}$ aryl; $C_5$-$C_8$ cycloalkyl; $C_6$-$C_{18}$ aryl having at least one $C_1$-$C_{20}$ alkyl substituent; $C_5$-$C_8$ cycloalkyl having at least one $C_1$-$C_{20}$ alkyl substituent; $C_4$-$C_{20}$ branched alkyl; or $C_2$-$C_{30}$ linear alkyl; and
- A is: N; P; S; or O; with the proviso that when A is S or O, $R_2$ is a nullity.

4. The process of claim 1, further comprising solvent.

5. The process of claim 1, wherein the addition reaction product comprises the Lewis acid connected to the Lewis base through saturated carbons that were previously the at least one olefin moiety.

6. The process of claim 1, wherein the addition product is a regioisomer.

7. The process of claim 1, further comprising heating.

8. The process of claim 1, or 2, wherein M is B.

9. The process of claim 1, or 3, wherein A is P.

10. The process of claim 1, further comprising purifying the addition reaction product.

11. The process of claim 1, wherein the addition reaction reagent is in gaseous form.

12. The process of claim 11, wherein the gaseous addition reaction reagent is purged through the fluid combination of (b) and (c).

13. The process of claim 11, wherein the reaction is placed under an atmosphere comprising the gaseous addition reaction reagent.

14. The process of claim 1, wherein the addition reaction reagent is ethylene, propylene, or 1-hexene.

15. The process of claim 2, wherein the addition reaction reagent is $CH_2$=$CHCH_2CH_2CH_2P(tBu)_2$ or $CH_2$=$CHCH_2CH_2CH_2P(C_6H_2Me_3)_2$.

16. The process of claim 1, wherein the sterically hindered Lewis acid is $B(C_6F_5)_3$.

17. The process of claim 1, wherein the sterically hindered Lewis base is $tBu_3P$.

18. The process of claim 1, wherein (a) is ethylene, (b) is $B(C_6F_5)_3$, (c) is $tBu_3P$, and the addition reaction product is $[tBu_3P(C_2H_4)B(C_6F_5)_3]$.

19. The process of claim 1, wherein (a) is propylene, (b) is $B(C_6F_5)_3$, (c) is $tBu_3P$, and the addition reaction product is $[tBu_3P(CH(Me)CH_2B(C_6F_5)_3]$.

20. The process of claim 1, wherein (a) is 1-hexene, (b) is $B(C_6F_5)_3$, (c) is $tBu_3P$, and the addition reaction product is $[tBu_3P(CH(C_4H_9)CH_2B(C_6F_5)_3]$.

21. The process of claim 2, wherein (a) is $CH_2=CHCH_2CH_2CH_2PR_2$, (b) is $B(C_6F_5)_3$,
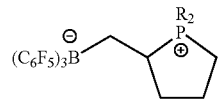
and the addition reaction product is, where the R of $PR_2$ is tBu or $C_6H_2Me_3$.
* * * * *